United States Patent
Nakatani et al.

(10) Patent No.: US 8,840,850 B2
(45) Date of Patent: Sep. 23, 2014

(54) FLOW CHANNEL STRUCTURE AND METHOD OF MANUFACTURING SAME

(75) Inventors: Masaya Nakatani, Hyogo (JP); Makoto Takahashi, Osaka (JP); Hiroshi Ushio, Osaka (JP); Takeki Yamamoto, Hyogo (JP)

(73) Assignee: Panasonic Corporation, Osaka (JP)

(*) Notice: Subject to any disclaimer, the term of this patent is extended or adjusted under 35 U.S.C. 154(b) by 317 days.

(21) Appl. No.: 13/131,893

(22) PCT Filed: Dec. 22, 2009

(86) PCT No.: PCT/JP2009/007119
§ 371 (c)(1),
(2), (4) Date: May 31, 2011

(87) PCT Pub. No.: WO2010/082279
PCT Pub. Date: Jul. 22, 2010

(65) Prior Publication Data
US 2011/0232794 A1 Sep. 29, 2011

(30) Foreign Application Priority Data

Jan. 15, 2009 (JP) ................................. 2009-006484
Mar. 19, 2009 (JP) ................................. 2009-067412

(51) Int. Cl.
*F16L 55/00* (2006.01)
*B05D 3/00* (2006.01)
(Continued)

(52) U.S. Cl.
CPC .............. *B01F 13/0059* (2013.01); *G01N 1/38* (2013.01); *B01F 2005/0632* (2013.01);
(Continued)

(58) Field of Classification Search
CPC ......... G01N 1/38; G01N 21/01; G01N 21/05; G01N 2021/0112; G01N 2021/0346; G01N 2021/05; B01L 3/502746; B01L 2200/12; B01L 2300/0816; B01L 2300/0877; B01L 2300/0887; B01L 2300/16; B01L 2300/0851; B01L 2300/0858; B01L 2300/0867; B01L 2400/086; B01L 2400/088; B01F 5/061; B01F 13/0061; B01F 13/0094; B01F 2005/0632; B01F 2500/0636; B81B 3/0078; B81B 3/0089; B81B 2201/051; B81B 2203/0338; B81C 1/00206
See application file for complete search history.

(56) References Cited

U.S. PATENT DOCUMENTS 7,290,667 B1 * 11/2007 Bakajin et al. ................ 210/503
2003/0119034 A1 6/2003 Kang et al.
(Continued)

FOREIGN PATENT DOCUMENTS

JP 2002-207031 7/2002
JP 2003/315349 11/2003
(Continued)

OTHER PUBLICATIONS
International Search Report issued Mar. 23, 2010 in International (PCT) Application No. PCT/JP2009/007119.
(Continued)

*Primary Examiner* — Jill Warden
*Assistant Examiner* — Timothy G Kingan
(74) *Attorney, Agent, or Firm* — Wenderoth, Lind & Ponack, L.L.P.

(57) ABSTRACT

A flow channel structure includes a substrate having a flow channel formed therein, and plural fibrous bristles extending from the inner wall of the flow channel. The flow channel is configured to allow a solution to flow through the flow channel. The inner wall of the flow channel is made of silicon. The flow channel is configured to allow a solution to flow through the flow channel. This flow channel structure can homogenize the solution inside the flow channel.

21 Claims, 15 Drawing Sheets

(51) Int. Cl.
*B32B 38/10* (2006.01)
*B01F 13/00* (2006.01)
*B81C 1/00* (2006.01)
*B01L 3/00* (2006.01)
*G01N 27/447* (2006.01)
*B81B 3/00* (2006.01)
*G01N 1/38* (2006.01)
*B01F 5/06* (2006.01)

(52) U.S. Cl.
CPC .. *B01F 2005/0636* (2013.01); *B01L 2300/0816* (2013.01); *B01F 5/061* (2013.01); *B01F 13/0091* (2013.01); *B81C 1/00206* (2013.01); *B81B 2203/0338* (2013.01); *B01L 2400/086* (2013.01); *B81B 2201/058* (2013.01); *B01L 2200/12* (2013.01); *B01L 2300/0887* (2013.01); *B01L 2300/16* (2013.01); *B01L 3/502746* (2013.01); *B01L 2300/0877* (2013.01); *G01N 27/44756* (2013.01); *B81B 3/0078* (2013.01); *B01L 2400/088* (2013.01)
USPC ............... 422/503; 422/82.05; 422/82.07; 422/82.08; 422/507; 137/3; 137/833; 137/834; 138/103; 156/279; 427/181; 427/237; 427/307

(56) References Cited

U.S. PATENT DOCUMENTS

| | | | |
|---|---|---|---|
| 2004/0175713 A1 | 9/2004 | Nakatani et al. | |
| 2005/0181195 A1* | 8/2005 | Dubrow | 428/297.4 |
| 2006/0159916 A1* | 7/2006 | Dubrow et al. | 428/357 |
| 2008/0056945 A1 | 3/2008 | Hattori | |
| 2008/0308529 A1 | 12/2008 | Nakatani et al. | |
| 2009/0250404 A1* | 10/2009 | Berkowitz et al. | 210/721 |
| 2010/0068822 A1* | 3/2010 | Heydenhauss et al. | 436/172 |
| 2010/0219488 A1 | 9/2010 | Nakatani et al. | |

FOREIGN PATENT DOCUMENTS

| | | | | |
|---|---|---|---|---|
| JP | 2004-033141 | | 2/2004 | |
| JP | 2005-139016 | | 6/2005 | |
| JP | 2006-045668 | | 2/2006 | |
| JP | 2006-145345 | A | 6/2006 | |
| JP | 2007-097510 | | 4/2007 | |
| JP | 2007-526439 | | 9/2007 | |
| JP | 2007-292527 | | 11/2007 | |
| TW | 200501277 | | 1/2005 | |
| WO | 02/23180 | | 3/2002 | |
| WO | 2004/099068 | | 11/2004 | |
| WO | 2005/123242 | | 12/2005 | |
| WO | WO 2008/064865 | * | 6/2008 | ........... B01L 3/00 |
| WO | 2009/034697 | | 3/2009 | |

OTHER PUBLICATIONS

Machine English translation of WO 02/23180, Mar. 2002.

Chinese Office Action, issued Jan. 22, 2013 in a Chinese application that is a foreign counterpart to the present application (with partial English translation).

* cited by examiner

FLOW CHANNEL STRUCTURE AND METHOD OF MANUFACTURING SAME

TECHNICAL FIELD

The present invention relates to a flow channel structure used for devices, such as chemical assay chips, having a fine flow channel, and also to a method of manufacturing the flow channel structure.

BACKGROUND ART

Flow channel structure is incorporated in chemical assay chips for analyzing glucide, lipid, blood, and protein, such as antigens and DNA.

FIG. 17 is a perspective view of conventional chemical assay chip 1 described in JP2007-292527A. The chemical assay chip is used for analyzing an antigen-antibody reaction for instance, and includes inlet port 2 for introducing an analyte solution including antigen, and flow channel 3 for transporting the introduced analyte solution to reaction region 4. The antigen in the transported analyte solution is reacted with antibody inside reaction region 4. After the reaction, the analyte solution is colored due to enzyme reaction or the like, and a concentration of the antigen is analyzed by measuring a degree of the coloration with a thermal lens microscope or the like.

In this type of chemical assay, it is necessary to thoroughly mix the solution, such as the analyte solution, in flow channel 3 and to obtain uniform distribution of the concentration. It becomes possible to accelerate the reaction in reaction region 4 or to improve the detecting accuracy in the detection region by homogenizing the solution in flow channel 3. However, the analyte solution may not become homogenized while the solution passes through flow channel 3 of chemical assay chip 1. If the analyte solution is not homogeneous, the reaction becomes slower or the detecting accuracy decreases, thereby resulting in degradation in performance of the chemical assay chip.

SUMMARY OF INVENTION

A flow channel structure includes a substrate having a flow channel formed therein, and plural fibrous bristles extending from the inner wall of the flow channel. The flow channel is configured to allow a solution to flow through the flow channel. The inner wall of the flow channel is made of silicon. The flow channel is configured to allow a solution to flow through the flow channel.

This flow channel structure can homogenize the solution inside the flow channel.

DETAIL DESCRIPTION OF PREFERRED EMBODIMENTS

Exemplary Embodiment 1

Figure 1A:
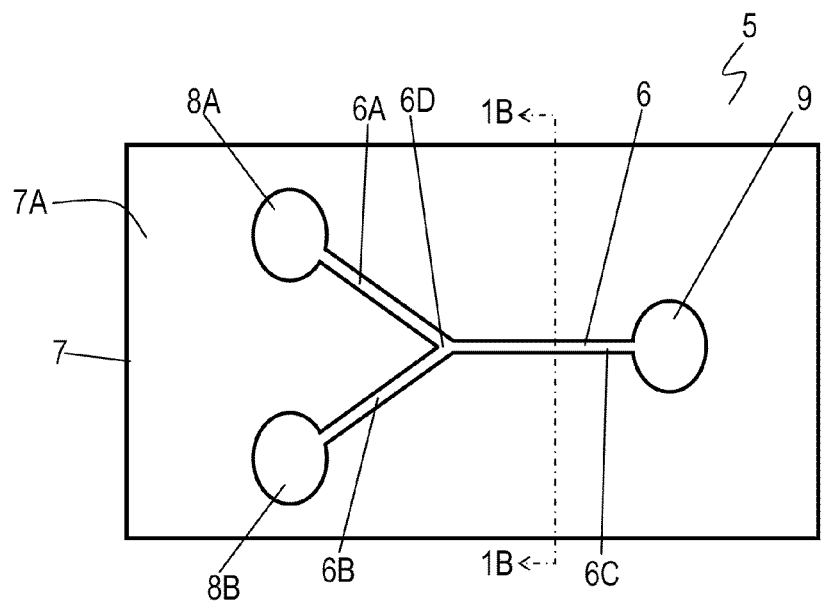
FIG. 1A is a plan view of a flow channel structure according to Exemplary Embodiment 1 of the present invention.

FIG. 1A is a top view of flow channel structure 5 according to Exemplary Embodiment 1 of the present invention. Flow channel structure 5 includes substrate 7 made of silicon. Substrate 7 has flow channel 6, inlet ports 8A and 8B and outlet port 9 formed in surface 7A. Flow channel 6 extends from inlet ports 8A and 8B to outlet port 9. More specifically, flow channel 6 includes inlet channels 6A and 6B and confluent flow channel 6C connected at connecting portion 6D. Inlet channel 6A extends from inlet port 8A to connecting portion 6D. Inlet channel 6B extends from inlet port 8B to connecting portion 6D. Confluent flow channel 6C extends from connecting portion 6D to outlet port 9.

Figure 1B:
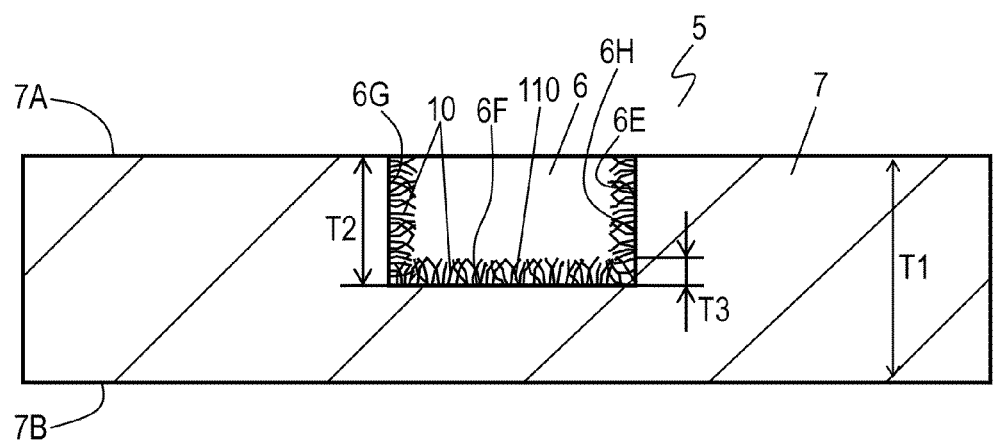
FIG. 1B is a sectional view of the flow channel structure taken along line 1B-1B shown in FIG. 1A.

FIG. 1B is a sectional view of flow channel structure 5 taken along line 1B-1B shown in FIG. 1A. Flow channel 6 has inner wall 6E made of silicon. Flow channel structure 5 further includes fibrous layer 110 having plural fibrous bristles 10 formed on inner wall 6E. The fibrous bristles 10 are bonded directly to inner wall 6E, and made of silicon dioxide. In other words, atoms or molecules composing substrate 7 and fibrous bristles 10 are covalently-bonded to each other. The area where inner wall 6E of substrate 7 is bonded to fibrous bristles 10 does not contain any materials, such as adhesive, other than the atoms or molecules that compose substrate 7 and fibrous bristles 10, but only the materials of inner wall 6E of substrate 7 and fibrous bristles 10. Substrate 7 has surface 7B opposite to surface 7A.

According to Embodiment 1, substrate 7 is made of single crystal silicon. However, substrate 7 may be made of either polycrystalline silicon or amorphous silicon as long as inner wall 6E of substrate 7 is made of silicon.

Substrate 7 has thickness T1 which is preferably not larger than 1 mm, and more preferably is about 500 μm according to Embodiment 1. Flow channel 6 has depth T2 of about 100 μm.

Figure 2:
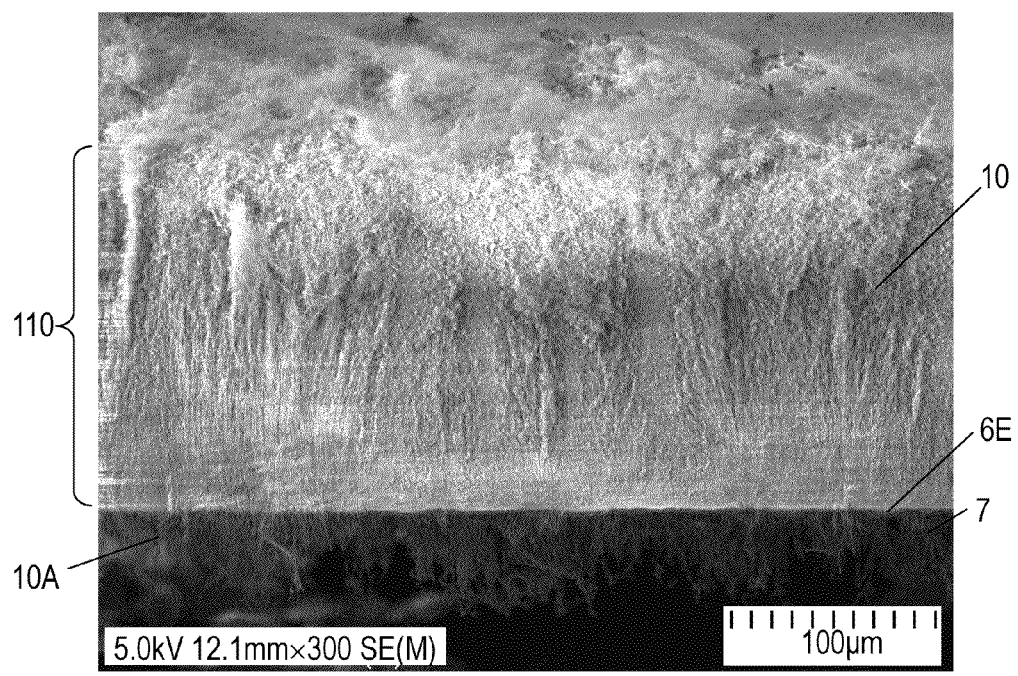
FIG. 2 is a sectional view of the flow channel structure according to Embodiment 1.

FIG. 2 is a sectional view of flow channel structure 5 at an area around inner wall 6E of flow channel 6. As shown in FIG. 2, fibrous bristle 10 may have portion 10A embedded in substrate 7 below inner wall 6E. This structure firmly bonds fibrous bristles 10 to substrate 7.

Figure 3:
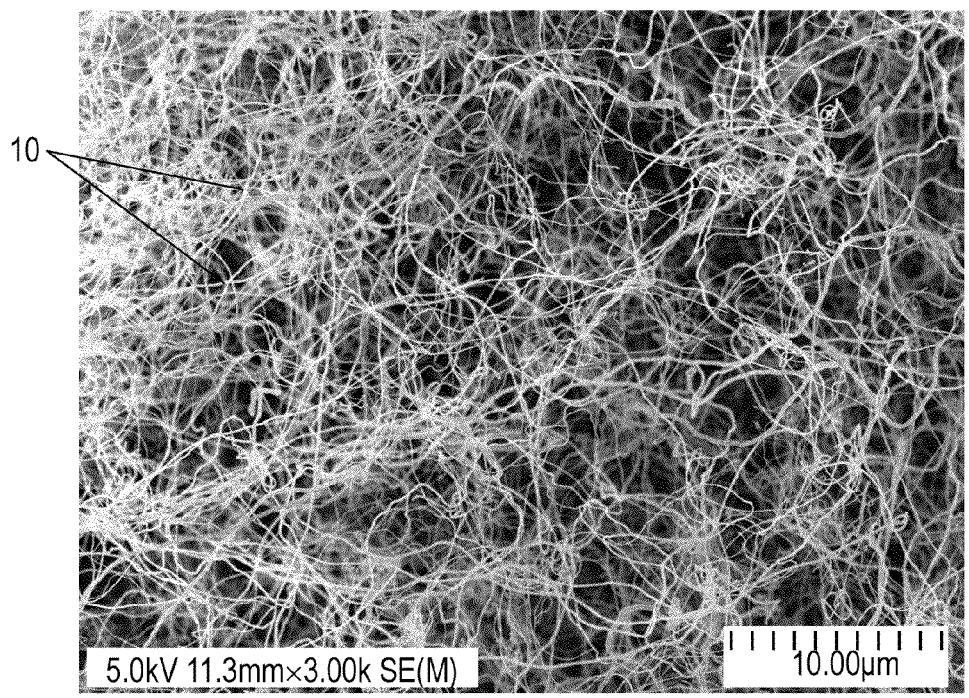
FIG. 3 is an enlarged view of fibrous bristles of the flow channel structure according to Embodiment 1.

FIG. 3 is an enlarged view of fibrous bristles 10 which is a microphotograph taken with a scanning electron microscope. Fibrous bristles 10 have total lengths ranging between 10 μm and 200 μm from inner wall 6E. Fibrous bristles 10 have kinked curled shapes and densely formed to tangle with one another, as shown in FIG. 3. In this case, the height T3 of fibrous layer 110 in flow channel 6 is about 30 μm.

Figure 4A:
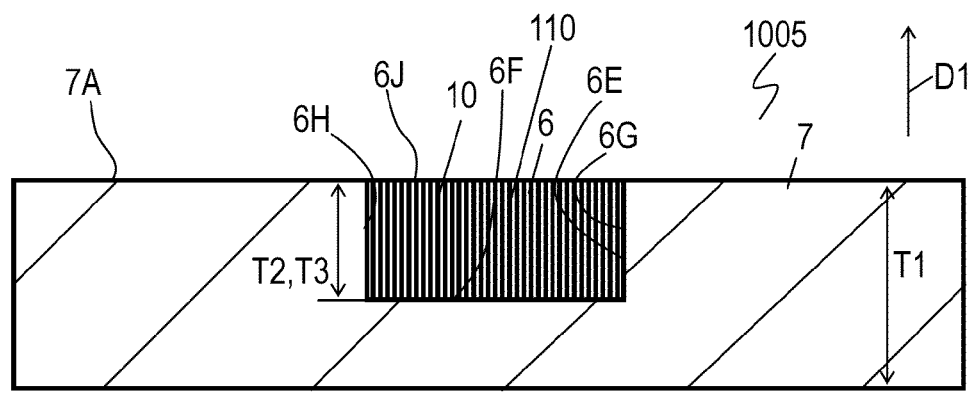
FIG. 4A is a sectional view of another flow channel structure according to Embodiment 1.
Figure 4B:
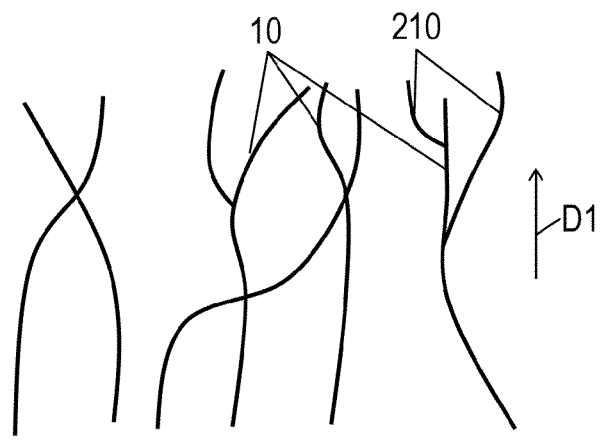
FIG. 4B is an enlarged view of the fibrous bristles of the flow channel structure shown in FIG. 4A.

FIG. 4A is a sectional view of another flow channel structure 1005 according to Embodiment 1. In FIG. 4A, components identical to those of flow channel structure 5 shown in FIGS. 1A and 1B are denoted by the same reference numerals. Flow channel 6 has opening portion 6J that opens to surface 7A of substrate 7. Inner wall 6E of flow channel 6 includes bottom 6F of flow channel 6 and sidewalls 6G and 6H extending from bottom 6F to surface 7A of substrate 7. Bottom 6F is located opposite to opening portion 6J. In flow channel structure 1005, fibrous bristles 10 extend in the same direction D1 from inner wall 6E of flow channel 6, which is direction D1 toward opening portion 6J from bottom 6F, such that fibrous layer 110 extends from bottom 6F to opening portion 6J of flow channel 6. Height T3 of fibrous layer 110 is thus the same as depth T2 of flow channel 6. FIG. 4B is an enlarged view of fibrous bristles 10 of flow channel structure 1005. The fibrous bristles 10 include fibrous bristles 10 that have separated twigs 210. The twigs 210 extend in directions different from direction D1. Fibrous bristles 10 having the twigs 210 separated and tangled with one another are connected firmly to one another to constitute fibrous layer 110.

The fibrous bristles 10 have diameters ranging from 0.01 μm to 10 μm, and are spaced from 0.001 μm to 10 μm.

Figure 5:
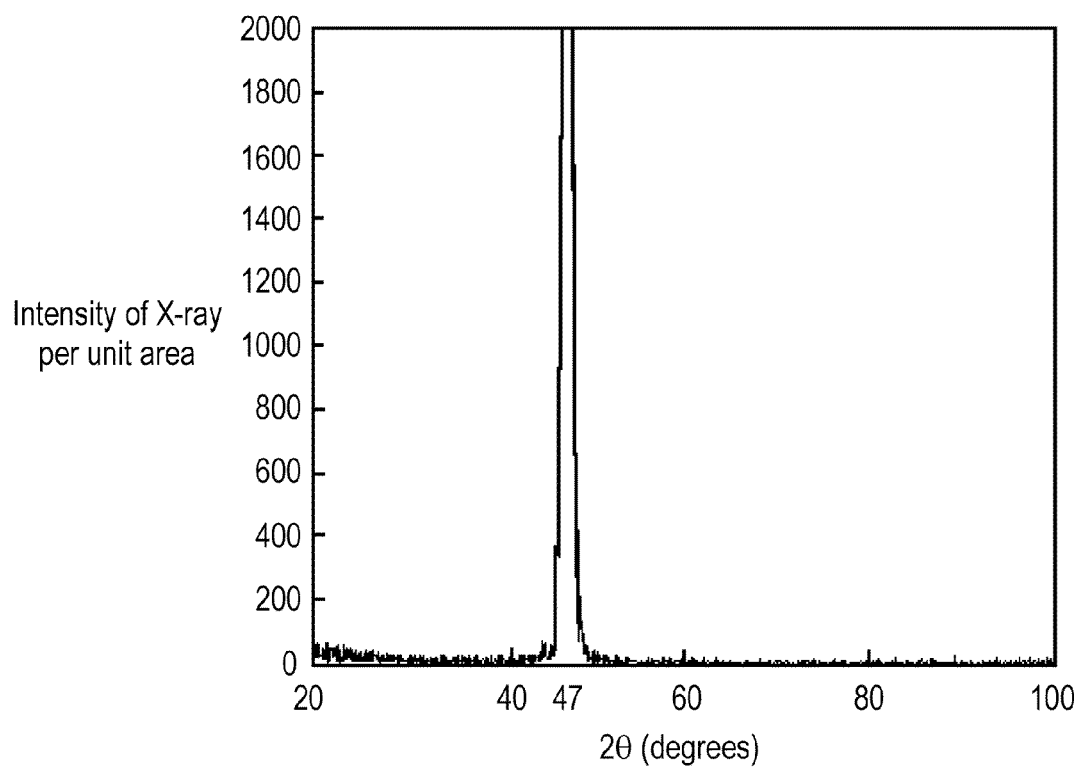
FIG. 5 shows a result of X-ray spectroscopic analysis of the fibrous bristles of the flow channel structure according to Embodiment 1.

FIG. 5 shows a result of X-ray spectroscopic analysis of fibrous layer 110 composed of fibrous bristles 10. It is considered that fibrous bristles 10 are made of amorphous silicon dioxide since no large peak other than the peak is observed in a region of about 47° in 2θ for silicon of (110) orientation in FIG. 5. Fibrous bristles 10 made of the amorphous silicon dioxide break less easily than fibrous bristles made of single-crystal silicon dioxide.

Figure 6:
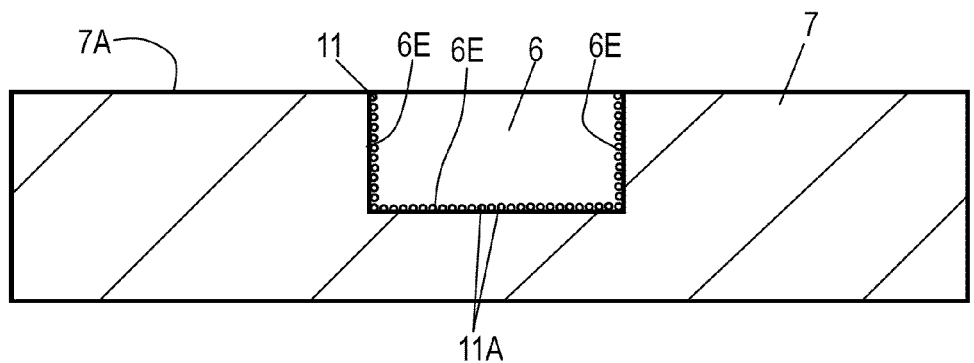
FIG. 6 is a sectional view of the flow channel structure according to Embodiment 1 for illustrating a process for manufacturing the channel structure.
Figure 7A:
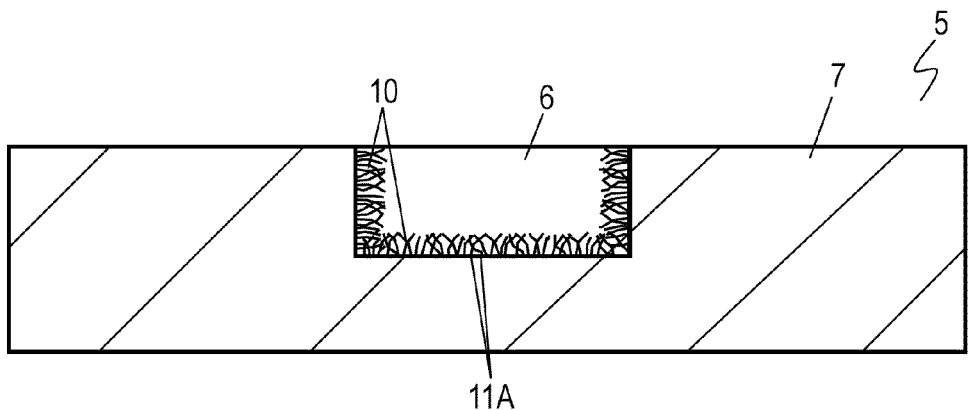
FIG. 7A is a sectional view of the flow channel structure according to Embodiment 1 for illustrating the process for manufacturing the channel structure.

A method of manufacturing flow channel structure 5 (1005) according to Embodiment 1 will be described. FIGS. 6 and 7A are sectional views of flow channel structure 5 for illustrating the method of manufacturing the structure.

A substrate having flow channel 6 formed in surface 7A by, e.g. an etching method is prepared. Metal, such as Pt, to function as a catalyst is deposited on inner wall 6E of flow channel 6 by a sputtering method, thereby forming catalyst layer 11. Catalyst layer 11 includes cores 11A, particles of Pt, scattered onto inner wall 6E. Inner wall 6E of flow channel 6 is partially exposed from between the cores 11A. The metal is not attached on surface 7A of substrate 7, thus disabling catalyst layer 11 to be formed on surface 7A. Catalyst layer 11 preferably has a thickness of about 20 nm. The thickness is controlled to control the diameter of fibrous bristles 10 and regulate a growing rate of fibrous bristles 10. Then, substrate 7 is put in a heating furnace which is heated with an atmosphere containing an inert gas, such as argon and oxygen, and is heated for a duration of 1000 minutes under conditions of a predetermined heating temperature ranging from 1000 to 1300° C. and a predetermined partial pressure of oxygen ranging from 1 to 1000 Pa. This heat treatment bonds the oxygen in the atmosphere with the silicon of inner wall 6E. The oxygen and the silicon form molecules of silicon dioxide by the heat treatment. The molecules of silicon dioxide are strung to respective ones of cores 11A of catalyst layer 11 to make fibrous bristles 10 on inner wall 6E of flow channel 6 by the heat treatment, as shown in FIG. 7A. Cores 11A of catalyst layer 11 exist in an area where fibrous bristles 10 bond to inner wall 6E in flow channel structure 5 shown in FIG. 7A. Alternatively, cores 11A of a portion of catalyst layer 11 are attached to the surfaces or insides of fibrous bristles 10. The predetermined heating temperature preferably ranges from 1100 and 1200° C., and the predetermined partial pressure of oxygen preferably ranges from 10 to 200 Pa from the point of view of productivity and heat resistance of fibrous bristles 10. Fibrous bristles 10 are bonded directly and firmly onto inner wall 6E since fibrous bristles 10 are made of the silicon in the surface of substrate 7, especially in inner wall 6E of flow channel 6 and the oxygen supplied during the heat treatment. A total pressure of the atmosphere is lower than the atmospheric pressure during the heat treatment, thereby causing fibrous bristles 10 to be short.

Fibrous bristles 10 grow in directions in which the oxygen diffuses during the heat treatment. The partial pressure of oxygen is raised to form the fibrous bristles 10 having curled shapes kinking to tangle with one another. The fibrous bristles 10 grow in the same direction if the partial pressure of oxygen is low. This process can form fibrous bristles 10 at high productivity.

Fibrous bristles 10 are not formed on surface 7A of silicon substrate 7 outside flow channel 6 in the heat treatment since catalyst layer 11 is not formed on surface 7A.

In the heat treatment, the partial pressure of oxygen in the atmosphere inside the furnace is kept as low as possible or no oxygen is included in the atmosphere until the temperature reaches from the initial temperature, or the room temperature, to the predetermined heat-treating temperature. Once the predetermined heat-treating temperature is reached and while this temperature is maintained, oxygen is injected into the atmosphere at the predetermined partial pressure which is higher than the pressure during the period of raising the temperature. Lengths of fibrous bristles 10 can be controlled within a range from 1 μm to 500 μm by this process. If the partial pressure of oxygen is set to the predetermined pressure mentioned above while raising the temperature of the furnace from the initial temperature to the heat-treating temperature, an excessive amount of oxygen forms an oxide film of silicon on inner wall 6E. This oxide film interferes with the growth of fibrous bristles 10 while the atmosphere is maintained at the predetermined heat-treating temperature.

Figure 7B:
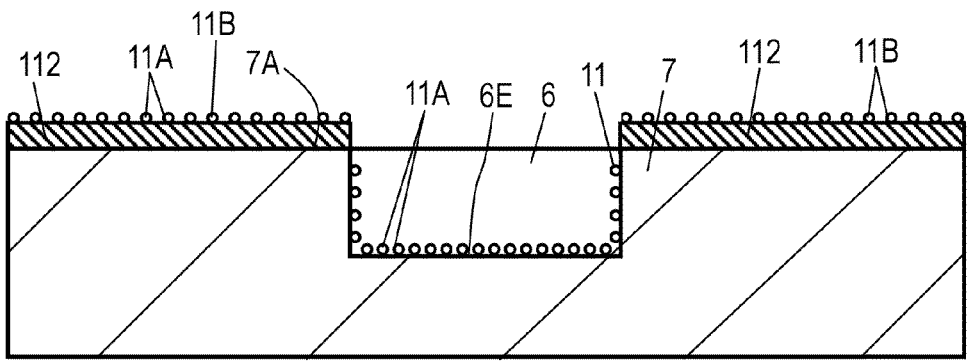
FIG. 7B is a sectional view of the flow channel structure shown in FIG. 7A, also illustrating the process for manufacturing the channel structure.

FIG. 7B is a sectional view of flow channel structure 5 for illustrating another method of manufacturing the structure 5. In FIG. 7B, components identical to those of substrate 7 shown in FIG. 6 are denoted by the same reference numerals. Oxide film 112 made of silicon dioxide is formed on surface 7A of substrate 7 of silicon to expose inner wall 6E of flow channel 6. Then, catalyst layers 11 and 11B are formed on inner wall 6E and oxide film 112 simultaneously, respectively, by depositing metal, such as Pt, to function as a catalyst by a sputtering method, as shown in FIG. 7B. Both catalyst layers 11 and 11B include cores 11A, particles of Pt, scattering on inner wall 6E and oxide film 112. Fibrous bristles 10 are not formed on oxide film 112 even if catalyst layer 11B is attached onto oxide film 112 since oxide film 112 prevents the growth of fibrous bristles 10. Alternatively, oxide film 112 may be formed selectively on any of bottom 6F, sidewalls 6G and 6H of inner wall 6E inside flow channel 6 so that fibrous bristles 10 can be formed only on a portion of inner wall 6E exposed from oxide film 112 since fibrous bristles 10 are not formed on the other portion of inner wall 6E covered by oxide film 112.

Alternatively, catalyst layer 11 may be formed only in a certain area of the surface of substrate 7 made of silicon. This allows fibrous bristles 10 to grow only in the area where catalyst layer 11 is formed while preventing fibrous bristles 10 from being formed in the other area on the surface of substrate 7 where catalyst layer 11 is not formed.

The metal used to form catalyst layer 11 can be metal, such as Fe, Co, Ni, and Au, besides Pt to provide for similar advantageous effect.

The manufacturing method of Embodiment 1 easily forms fibrous bristles 10 not only on bottom 6F of inner wall 6E but also sidewalls 6G and 6H of flow channel 6 as described above.

FIGS. 8A, 8B, 9, 10A and 10B are sectional views of flow channel structure 5 for illustrating a further method of manufacturing structure 5 according to Embodiment 1. In FIGS. 8A, 8B, 9, 10A and 10B, components identical to those of substrate 7 shown in FIG. 6 are denoted by the same reference numerals.

Figure 8A:
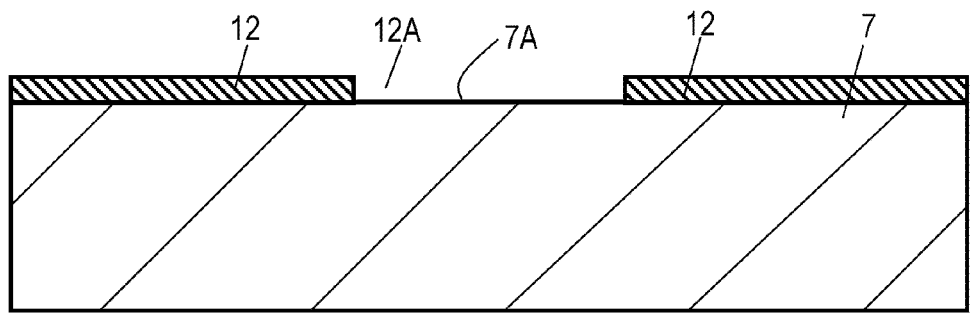
FIG. 8A is a sectional view of the flow channel structure according to Embodiment 1 for illustrating another process for manufacturing the channel structure.
Figure 8B:
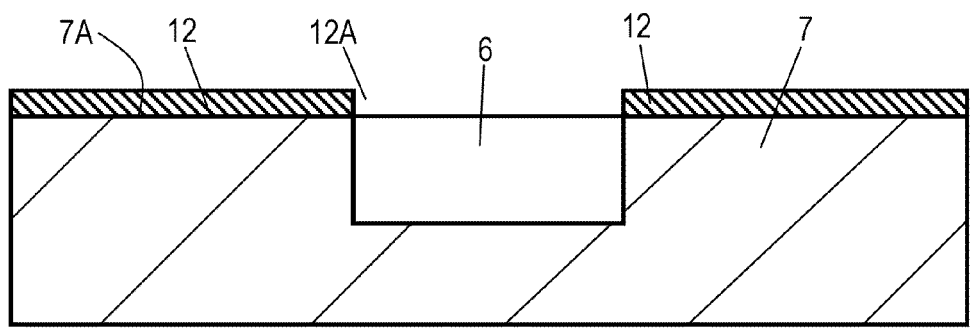
FIG. 8B is a sectional view of the flow channel structure shown in FIG. 8A for illustrating the process for manufacturing the channel structure.

First, surface 7A of substrate 7 is covered with protective layer 12, as shown in FIG. 8A. Protective layer 12 is made of silicon dioxide or resin, such as photoresist. Protective layer 12 has opening 12A where flow channel 6 is formed. Substrate 7 is dry-etched by blasting an etching gas to facilitate etching and another gas to suppress the etching alternately against surface 7A of substrate 7 from the outside of protective layer 12 through opening 12A, thereby forming flow channel 6 in surface 7A of substrate 7, as shown in FIG. 8B. The etching gas used here can be at least one selected from $SF_6$, $CF_4$, $NF_3$ and $XeF_2$. The gas for suppressing the etching can be $CHF_3$ or $C_4F_8$.

Figure 9:
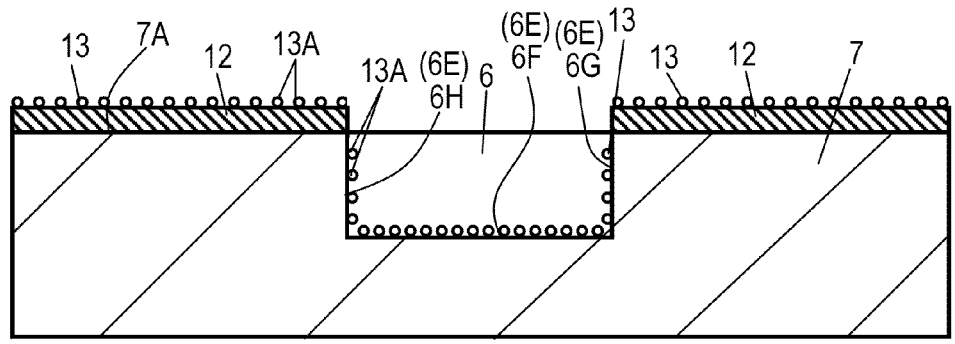
FIG. 9 is a sectional view of the flow channel structure shown in FIG. 8A for illustrating a process for manufacturing the channel structure.

Next, seed layer 13 is formed on inner wall 6E, as shown in FIG. 9, by decomposing at least one kind of gas of $CF_4$, $CHF_3$, $C_2F_6$, $C_3F_8$, and $C_4F_8$ in an atmosphere of plasma and introducing the gas into flow channel 6. When protective layer 12 masks surface 7A of substrate 7 and selectively exposes inner wall 6E of flow channel 6, the gas is introduced into flow channel 6, thereby forming seed layer 13 on both inner wall 6E of flow channel 6 and protective layer 12. After the formation of flow channel 6, additional protective layer may be formed partially on inner wall 6E of flow channel 6 by using the same material as protective layer 12 so that fibrous bristles 10 can be formed only in a certain area of inner wall 6E. In other words, fibrous bristles 10 can be formed only in the area of inner wall 6E exposed from the protective layer by forming the protective layer on any of bottom 6F, sidewalls 6G and 6H of inner wall 6E of flow channel 6, while fibrous bristles 10 are not formed in the area of inner wall 6E covered by the protective layer.

Seed layer 13 includes plural cores 13A made of organic polymer containing C and F elements, and it can be formed by decomposing fluorocarbon gas, such as $CF_4$, $CHF_3$, $C_2F_6$, $C_3F_8$, and $C_4F_8$ in an atmosphere of plasma by a plasma-activated CVD method. Seed layer 13 can be formed easily and uniformly by decomposing the above gas in the atmosphere of inductively coupled plasma (ICP) which facilitates the decomposition of the gas.

Figure 10A:
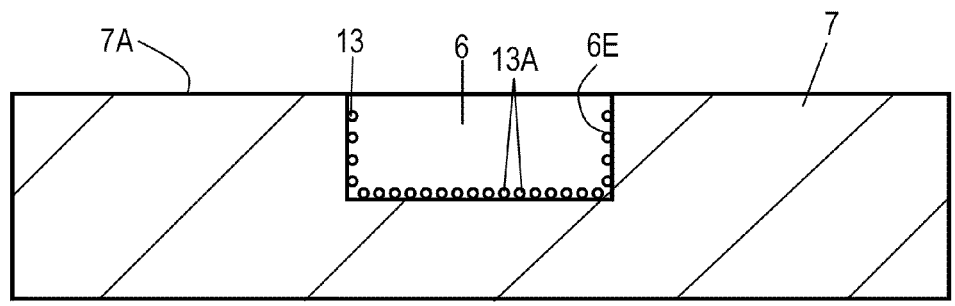
FIG. 10A is a sectional view of the flow channel structure shown in FIG. 8A for illustrating the process for manufacturing the channel structure.

Next, protective layer 12 is removed by a chemical treatment using an agent, as shown in FIG. 10A. Since seed layer 13 formed by the plasma-activated CVD method has a comparatively high resistance to chemical agent, only protective layer 12 is selectively removed easily.

Figure 10B:
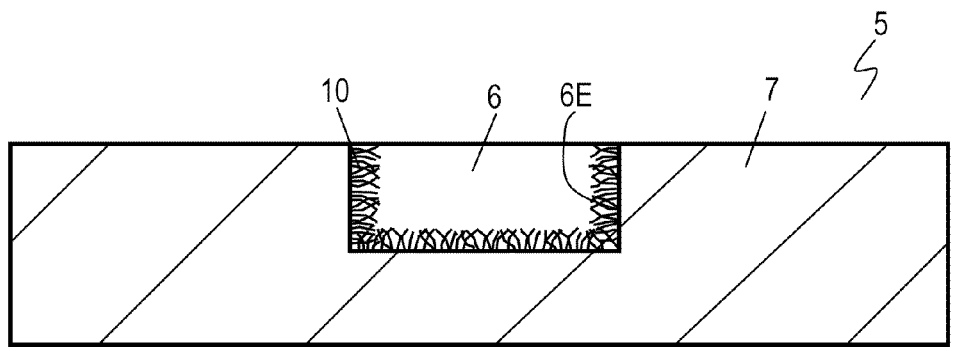
FIG. 10B is a sectional view of the flow channel structure shown in FIG. 8A for illustrating the process for manufacturing the channel structure.

Then, fibrous bristles 10 of silicon dioxide are formed in the area of inner wall 6E of flow channel 6 where seed layer 13 is formed, as shown in FIG. 10B, by heating substrate 7 at a heat-treatment temperature ranging from 1000 to 1100° C. in an atmosphere containing oxygen. This method bonds fibrous bristles 10 directly and firmly to inner wall 6E of silicon in flow channel 6 of substrate 7, accordingly providing fibrous bristles 10 with outstanding heat resistance and preventing fibrous bristles 10 from being removed easily.

Inner wall 6E of substrate 7 may be covered with a very thin layer of naturally-formed oxide film although inner wall 6E is preferably made of pure silicon. Alternatively, inner wall 6E of substrate 7 may be covered with a very thin oxide film resulting from the heat treatment. Fibrous bristles 10 can be bonded directly and firmly to inner wall 6E even when any of such thin oxide films is formed on inner wall 6E.

Fibrous bristles 10 grow by stringing molecules made of silicon dioxide strung and extending from cores 13A of seed layer 13, and prevent any materials other than silicon dioxide from being contained in fibrous bristles 10, thus having a composition containing few impurities. Since the above heat treatment burns up seed layer 13 (e.g., cores 13A) consisting of C and F, seed layer 13 does not remain on inner wall 6E, thereby providing inner wall 6E of flow channel 6 in flow channel structure 5 shown in FIG. 10B with a hydrophilic property.

Figure 10C:
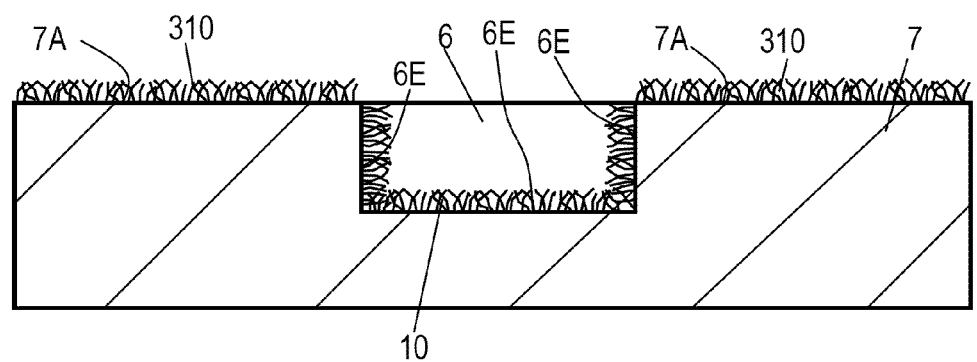
FIG. 10C is a sectional view of the flow channel structure according to Embodiment 1 for illustrating still another process for manufacturing the channel structure.
Figure 10D:
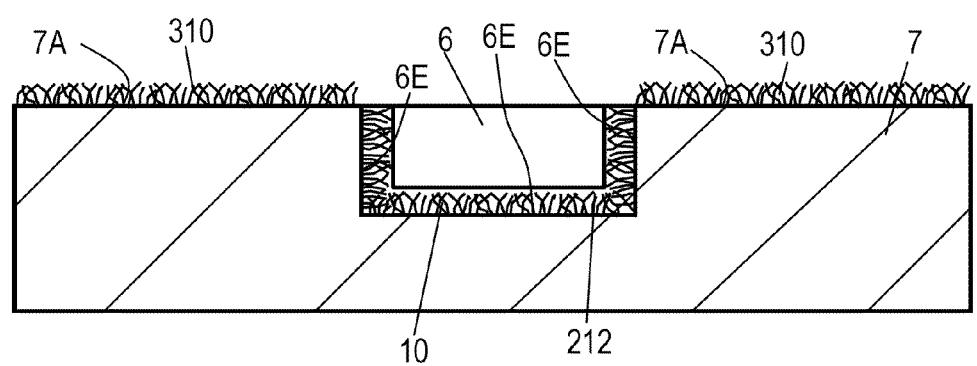
FIG. 10D is a sectional view of the flow channel structure shown in FIG. 10C for illustrating the process for manufacturing the channel structure.
Figure 10E:
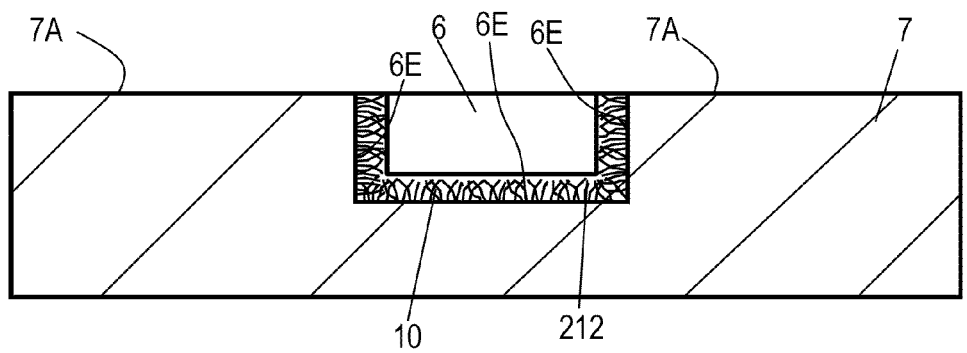
FIG. 10E is a sectional view of the flow channel structure shown in FIG. 10C for illustrating the process for manufacturing the channel structure.
Figure 10F:
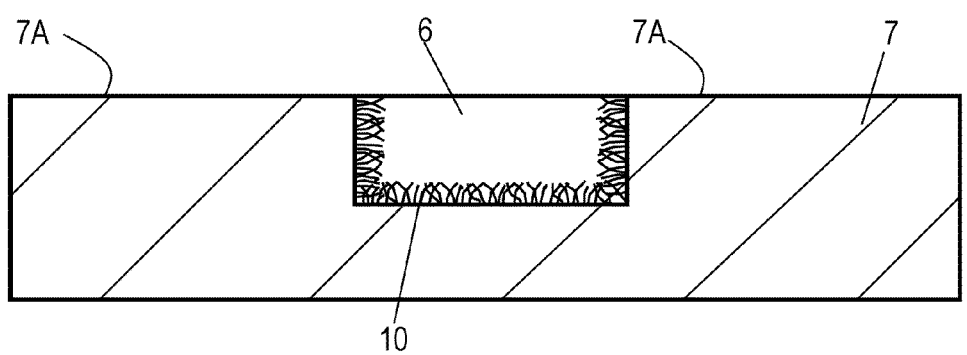
FIG. 10F is a sectional view of the flow channel structure shown in FIG. 10C for illustrating the process for manufacturing the channel structure.

FIGS. 10C to 10F are sectional views of flow channel structure 5 for illustrating a further method of manufacturing the flow channel structure. First, fibrous bristles 10 and 310 are formed on inner wall 6E of flow channel 6 and surface 7A of substrate 7, respectively, as shown in FIG. 10C, using catalyst layer 11 or seed layer 13. After that, protective layer 212 made of, e.g. resin is formed on inner wall 6E to completely cover only fibrous bristles 10 out of fibrous bristles 10 and 310, but to expose fibrous bristles 310 on surface 7A from protective layer 212, as shown in FIG. 10D. After that, fibrous bristles 310 exposed from protective layer 212 are etched and removed using ordinary etching solution, such as hydrofluoric acid (HF) or buffered hydrofluoric acid (BHF), as shown in FIG. 10E. Then, protective layer 212 is removed, as shown in FIG. 10F. This method forms no oxide film on the exposed surface 7A.

This method removes protective layer 212 preferably by a chemical treatment using a solvent. A mechanical process, such as grinding, to remove protective layer 212 causes damages to fibrous bristles 10.

In the heat treatment to form fibrous bristles 10, the atmosphere may contain water vapor in addition to oxygen and inert gas. This allows fibrous bristles 10 to grow fast.

Figure 11:
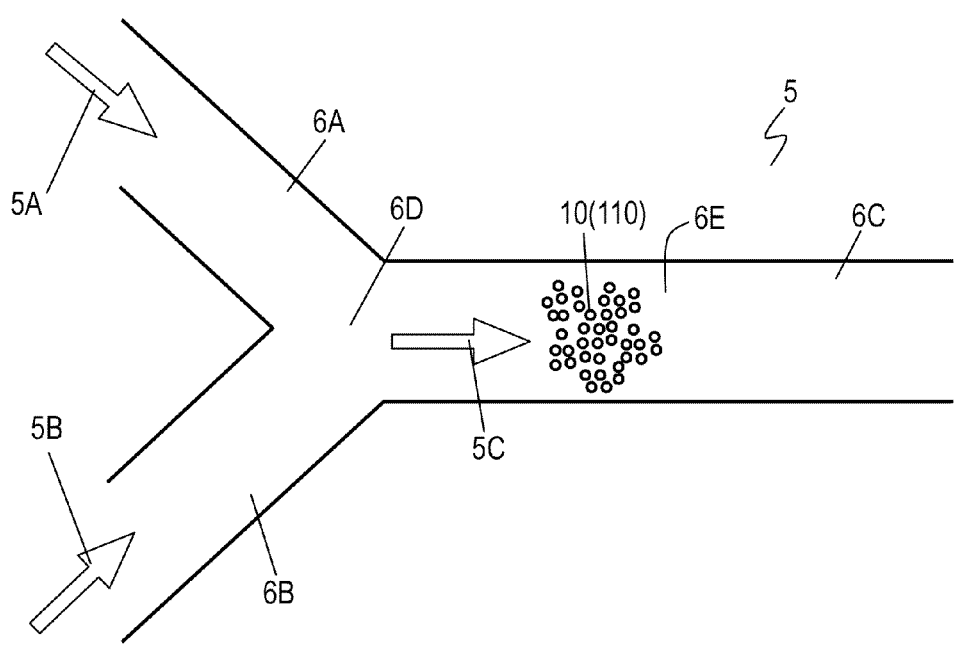
FIG. 11 is a schematic top view of the flow channel structure according to Embodiment 1.

An operation of flow channel structure 5 according to Embodiment 1 will be described below. FIG. 11 is a schematic top view of flow channel structure 5. Confluent flow channel 6C of flow channel 6 has fibrous layer 110 including plural fibrous bristles 10 formed on inner wall 6E. Different solutions 5A and 5B, such as analyte solutions, are introduced into inlet channels 6A and 6B of flow channel 6 from inlets 8A and 8B, respectively, shown in FIG. 1B. Solutions 5A and 5B are mixed together at connecting portion 6D to become solution 5C. Solution 5C is transferred to outlet port 9 through confluent flow channel 6C. Any of solutions 5A, 5B, and 5C may be a watery form having a low viscosity or a gelatinous form having a high viscosity. The fibrous bristles 10 formed on confluent flow channel 19 can homogenize mixed solution 5C. If the fibrous bristles 10 are not provided, connecting portion 6D may produce a laminar flow that prevents solutions 5A and 5B from being mixed well.

In flow channel structure 5 of Embodiment 1, fibrous bristles 10 are provided at a portion along confluent flow channel 6C, but may be formed at connecting portion 6D.

The fibrous bristles 10 disperse directions in which solution 5C flows in confluent flow channel 6C (flow channel 6) in different directions. This function facilitates molecules that compose solution 5C to become mixed homogeneously, thereby improving the homogeneity of solution 5C in flow channel 6.

Figure 17:
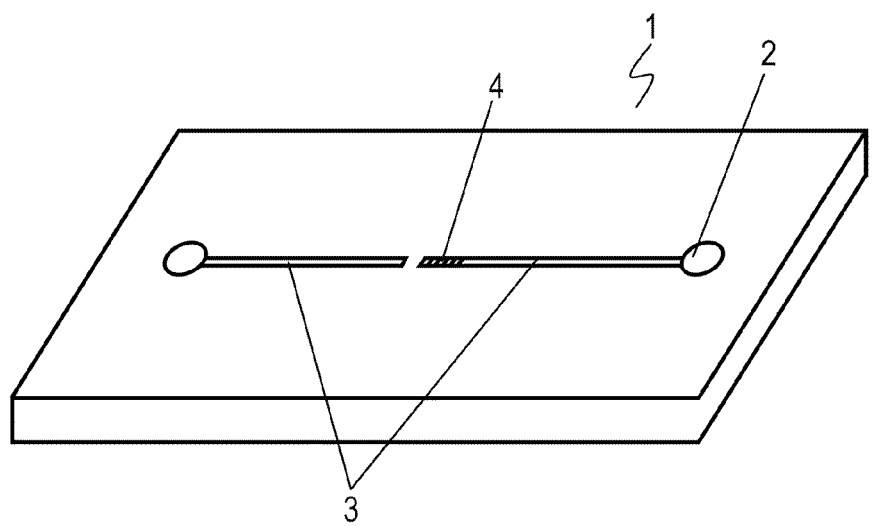
FIG. 17 is a perspective view of a conventional chemical assay chip.

A chemical assay chip equipped with flow channel structure 5 causes an analyte solution transferred through flow channel 6 of flow channel structure 5 to react in a reaction region, or detects the analyte solution delivered through flow channel 6 of flow channel structure 5 after the reaction at a detection region. The conventional chemical assay chip 1 shown in FIG. 17 does not mix analyte solutions homogeneously and suppresses the reaction or lowers the detecting accuracy, accordingly degrading the performance of chemical assay chip 1. On the other hand, flow channel structure 5 of Embodiment 1 homogenizes solutions, such as analyte solutions to accelerate the reaction and improve the detecting accuracy.

In flow channel structure 5, fibrous bristles 10 are made of silicon dioxide having a high hydrophilic property. This structure facilitates solution 5C to flow and spread quickly along side surfaces of fibrous bristles 10, hence preventing bubbles from developing while the solution flows in flow channel 6.

In the case that substrate 7 includes a silicon substrate made of silicon, flow channel 6 can be processed to have a fine and complicated shape. Silicon, however, has a hydrophobic property having little affinity to water and tends to produce bubbles. Fibrous bristles 10 having a high hydrophilic property formed in flow channel 6 prevent flow channel structure 5 of Embodiment 1 from producing bubbles in flow channel 6.

Fibrous bristles 10 made of amorphous silicon dioxide have curled shapes tangling with one another, and change the flow of solution 5C randomly. In addition, stress applied by the flow of solution 5C to fibrous bristles 10 is dispersed, and hence, fibrous bristles 10 are prevented from easily breaking.

In flow channel structure 5 according to Embodiment 1, fibrous bristles 10 can be formed easily at a desired density on any portion, such as bottom 6F, sidewalls 6G and 6H, of inner wall 6E inside flow channel 6. Since a frictional property of inner wall 6E of flow channel 6 is variable depending on the density and length of fibrous bristles 10, a resistance exerted on solution 5C by inner wall 6E can be controlled arbitrarily, and a velocity of solution 5C flowing in flow channel 6 can be adjusted. In flow channel structure 5 shown in FIG. 1, the resistance exerted on solution 5C by inner wall 6E changes uniformly to allow solution 5C to flow steadily since fibrous bristles 10 are formed uniformly on bottom 6F and sidewalls 6G and 6H of flow channel 6.

In flow channel structure 5 of Embodiment 1, flow channel 6 has an extremely large surface area with the fibrous bristles 10. This structure allows a large amount of reactant to be bonded to fibrous bristles 10, and facilitates the reaction between solution 5C and the reactant.

In flow channel structure 1005 shown in FIG. 4A, flow channel 6 is provided with fibrous layer 110 including the fibrous bristles 10 extending up to opening portion 6J of flow channel 6. In flow channel structure 1005, fibrous layer 110 also functions as a filter for removing foreign particles in the solution that flows in flow channel 6.

Figure 12:
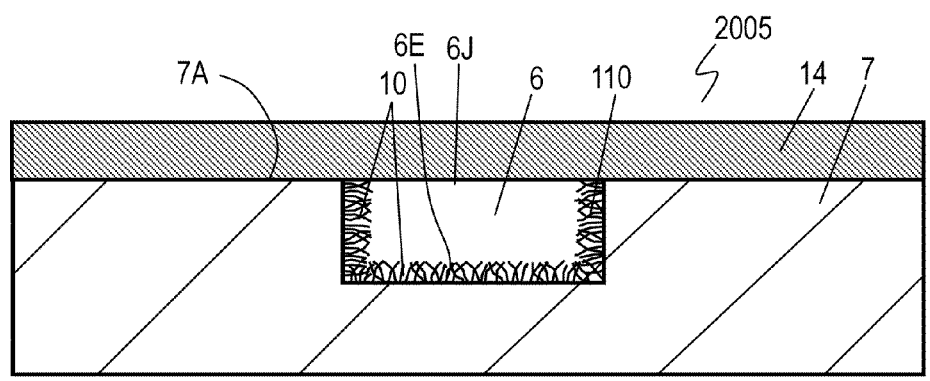
FIG. 12 is a sectional view of another flow channel structure according to Embodiment 1.

FIG. 12 is a sectional view of another flow channel structure 2005 according to Embodiment 1. In FIG. 12, components identical to those of flow channel structure 5 shown in FIGS. 1A and 1B are denoted by the same reference numerals. Flow channel structure 2005 further includes lid substrate 14 disposed on surface 7A of substrate 7 of flow channel structure 5 shown in FIGS. 1A and 1B. Lid substrate 14 covers opening portion 6J of flow channel 6. Inlet ports 8A and 8B and outlet port 9 shown in FIG. 1A face the outside of flow channel structure 2005.

Surface 7A of substrate 7 is smooth without having fibrous bristles 10 formed thereon, and allows lid substrate 14 to contact surface 7A of substrate 7 securely. Lid substrate 14 is preferably bonded to surface 7A of substrate 7 by a method, such as a direct bonding or an anodic bonding without using any adhesive. Such bonding methods prevent an impairment of a light-transmittable property due to the adhesive and a defect in shape of flow channel 6 due to squeeze-out of the adhesive.

Lid substrate 14 may be made of an optically-transmittable material that allows the solution flowing in flow channel 6 to be measured optically. The light-transmittable material can be selected easily from a group consisting of glass, quartz, and sapphire according to a wavelength of light used for the measurement. As stated, the present invention does not place any restriction on the material of lid substrate 14 and the manufacturing method thereof.

Figure 13:
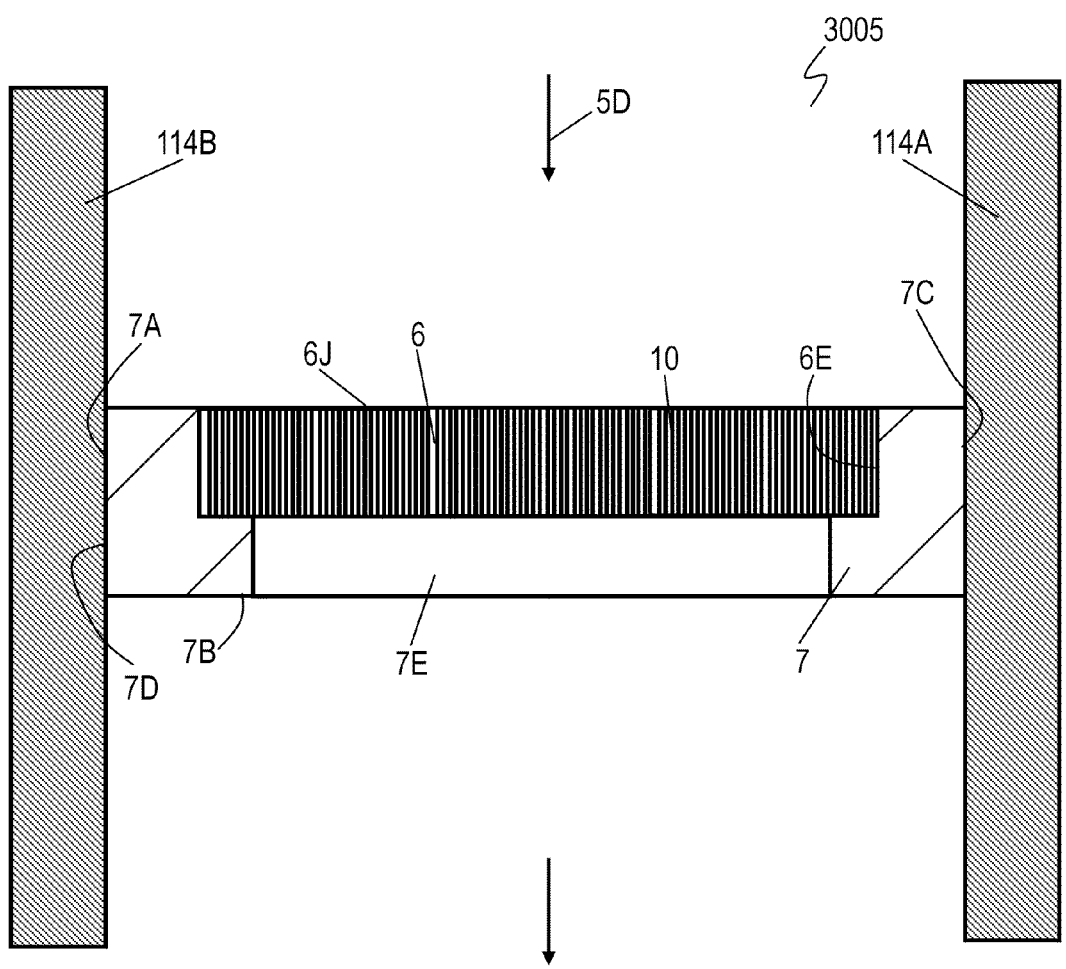
FIG. 13 is a sectional view of still another flow channel structure according to Embodiment 1.

FIG. 13 is a sectional view of further flow channel structure 3005 according to Embodiment 1. In FIG. 13, components identical to those of flow channel structure 1005 shown in FIG. 4A are denoted by the same reference numerals. In flow channel structure 3005, solution 5D flows in a direction parallel to the fibrous bristles 10 from opening portion 6J of flow channel 6 formed in surface 7A of substrate 7. In other words, fibrous bristles 10 extend in the same direction as a direction in which solution 5D flows in flow channel 6. Recess 7E is formed in surface 7B by etching substrate 7 from surface 7B to bottom 6F of flow channel 6 after fibrous bristles 10 are formed on bottom 6F of flow channel 6. The fibrous bristles 10 are tangled up partially with one another, and can be retained on substrate 7 without being removed from the bottom of recess 7E even though fibrous bristles 10 extend substantially in the same direction.

Substrate 7 has side surfaces 7C and 7D which are perpendicular to surfaces 7A and 7B. Flow channel structure 3005 further includes sidewall substrates 114A and 114B bonded to side surfaces 7C and 7D of substrate 7, respectively. Solution 5D flows between sidewall substrates 114A and 114B and along sidewall substrates 114A and 114B. Sidewall substrates 114A and 114B can completely seal flow channel structure 3005 while fibrous bristles 10 protrude from opening portion 6J of substrate 7.

Flow channel structure 3005 includes fibrous bristles 10 extending along the flowing direction of solution 5D between sidewall substrates 114A and 114B, hence improving the homogeneity of solution 5D while keeping a low resistance of the flow channel, in addition to its function as a filter for removing foreign particles in solution 5D.

Exemplary Embodiment 2

Figure 14:
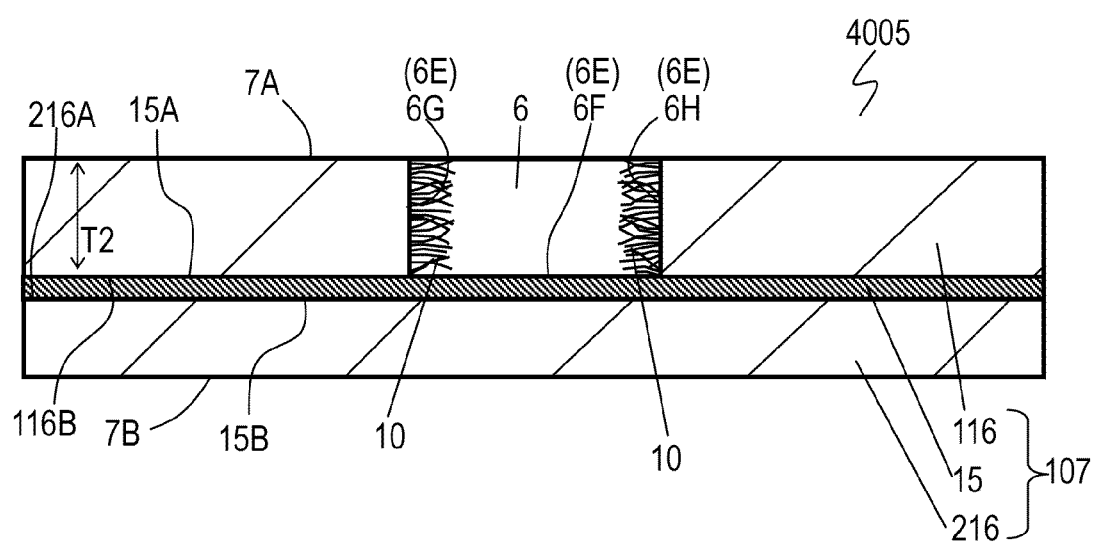
FIG. 14 is a sectional view of a flow channel structure according to Exemplary Embodiment 2 of the invention.

FIG. 14 is a sectional view of flow channel structure 4005 according to Exemplary Embodiment 2 of the present invention. In FIG. 14, components identical to those of flow channel structure 5 shown in FIGS. 1A and 1B are denoted by the same reference numerals. Flow channel structure 4005 includes substrate 107 instead of substrate 7 of flow channel structure 5 shown in FIG. 1B. Substrate 107 is a Silicon-On-Insulator (SOI) substrate that includes silicon layers 116 and 216 made of silicon, and silicon dioxide layer 15 placed between silicon layers 116 and 216. Silicon layer 116 has surface 7A and surface 116B opposite to surface 7A. Silicon dioxide layer 15 has surface 15A situated on surface 116B of silicon layer 116 and surface 15B opposite to surface 15A. Silicon layer 216 has surface 216A situated on surface 15B of silicon dioxide layer 15 and surface 7B opposite to surface 216A.

According to Embodiment 2, flow channel structure 4005 is provided with flow channel 6 formed in surface 7A of substrate 107 similarly to flow channel structure 5 of Embodiment 1 shown in FIG. 1B. To be more specific, flow channel 6 is formed by etching surface 7A of substrate 107 similarly to substrate 7 shown in FIG. 8A. The etching is processed from surface 7A to silicon dioxide layer 15. That is, silicon dioxide layer 15 stops the etching to make depth T2 of flow channel 6 equal to the thickness of silicon layer 16. This allows depth T2 of flow channel 6 to be constant easily.

In flow channel structure 4005, silicon dioxide layer 15 is exposed in bottom 6F of inner walls 6E inside flow channel 6 so that bottom 6F is made of silicon dioxide. On the other hand, silicon layer 16 is exposed in sidewalls 6G and 6H of inner walls 6E, so that sidewalls 6G and 6H are made of silicon. Fibrous bristles 10 can be formed selectively on the surfaces of flow channel 6 made of silicon since they are formed on surfaces made of silicon but not on surfaces made of silicon dioxide.

In flow channel structure 4005, bottom 6F of flow channel 6 has surface 15A of silicon dioxide layer 15 having a high hydrophilic property. Sidewalls 6G and 6H are covered with fibrous bristles 10 made of the silicon dioxide also having a high hydrophilic property. This structure reduces bubbles developing while the solution flows in flow channel 6.

Exemplary Embodiment 3

Figure 15:
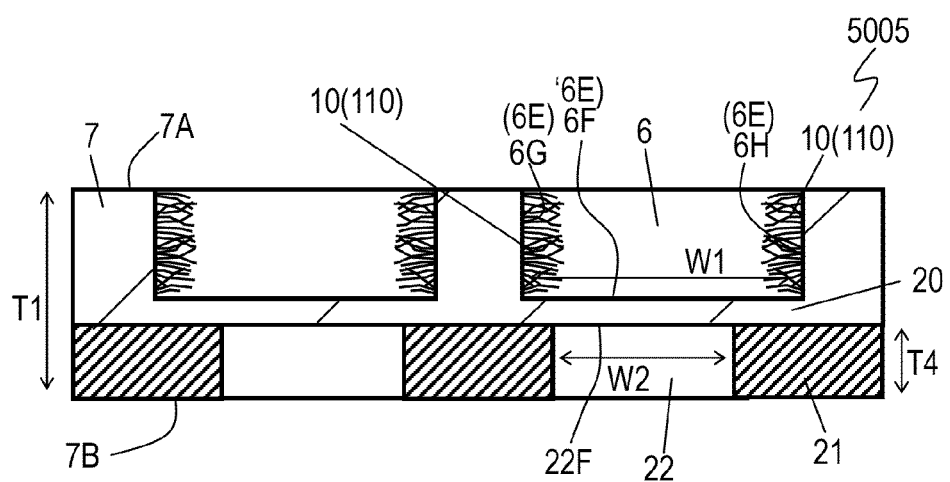
FIG. 15 is a sectional view of a flow channel structure according to Exemplary Embodiment 3 of the invention.

FIG. 15 is a sectional view of flow channel structure 5005 according to Exemplary Embodiment 3 of the present invention. In FIG. 15, components identical to those of flow channel structure 5 shown in FIG. 1B are denoted by the same reference numerals. In flow channel structure 5005, substrate 7 is provided with cavity 22 in surface 7B thereof. Cavity 22 is formed in a position opposite to flow channel 6 provided in surface 7A. Substrate 7 includes bottom plate portion 20 that constitutes bottom 6F of flow channel 6. Flow channel 6 faces bottom 22F of cavity 22 across bottom plate portion 20. Substrate 7 is light-transmittable, or at least bottom plate portion 20 is light-transmittable. Substrate 7 has base portion 21 provided around cavity 22.

Plural fibrous bristles 10 are formed on sidewalls 6G and 6H of inner walls 6E in flow channel 6, but not on bottom 6F.

Since the bottom surface of bottom plate portion 20, or bottom 22F of cavity 22 is exposed optically, reactivity to light of any substance, such as cells, inside flow channel 6 can be measured easily with light, especially of the light of a penetrable spectrum through bottom plate portion 20.

In flow channel structure 5005, a substance can be observed optically with light that penetrates the substance and reaches cavity 22 by passing through bottom plate portion 20 from opening portion 6J of flow channel 6. The substance can also be observed optically with light that enters from cavity 22, passes through bottom plate portion 20, and returns to cavity 22 by passing through bottom plate portion 20 after being reflected by the substance. As discussed above, flow channel structure 5005 is useful to observe substance in various manners depending on whether the substance being observed passes light or reflects the light.

Base portion 21 provided around cavity 22 supports flow channel structure 5005 and improves a physical strength of flow channel structure 5005. Base portion 21 allows light-transmittable plate portion 20 to be thin, and decreases attenuation of light in bottom plate portion 20, accordingly increasing the light transmittance. Base portion 21 of substrate 7 can be made of material, such as single crystal silicon or polycrystalline silicon, and can be processed finely.

Substrate 7 has thickness T1 ranging from 100 μm to 800 μm. Base portion 21 has thickness T4 ranging from 100 μm to 500 μm. The sum of the thickness of bottom plate portion 20 and the depth of flow channel 6 ranges from 0.1 μm to 300 μm. The depth of flow channel 6 is larger than thickness T4 of base portion 21 to provide a larger reaction path. The thickness of base portion 21 may be larger than the depth of flow channel 6, that is, bottom plate portion 20 is thin, and base portion 21 can reinforce substrate 7.

Width W1 of flow channel 6 and width W2 of cavity 22 range from 100 nm to 300 μm. Widths W1 and W2 of flow channel 6 and cavity 22 allow light to pass through. Width W1 of flow channel 6 may be larger than width W2 of cavity 22 so as to allow the substance in flow channel 6 to be observed easily with light entering from opening portion 6J into flow channel 6. Width W2 of cavity 22 may be larger than width W1 of flow channel 6, on the other hand, so as to allow the substance to be observed easily with light passing through bottom plate portion 20 from cavity 22.

Surfaces 7A and 7B of substrate 7 may be etched to form flow channel 6 and cavity 22, respectively, thereby providing flow channel structure 5005. Alternatively, base portion 21 may be bonded to a substrate having flow channel 6 and bottom plate portion 20 formed unitarily, thereby providing flow channel structure 5005. Further, a substrate having a through-hole formed in an area of flow channel 6 may be bonded to base portion 21 and another substrate having a light-transmittable property and constituting the bottom plate portion to close the through-hole, thereby providing flow channel structure 5005.

Bottom plate portion 20 may preferably essentially contain silicon dioxide, but may be made of any other material, such as glass, quartz, sapphires, or light-transmittable resin, having a light-transmittable property.

Width W1 of flow channel 6 may be larger than width W2 of cavity 22 so as to allow base portion 21 to have a large size, and provides substrate 7 with a large physical strength, so as to provide flow channel structure 5005 with stability.

Figure 16A:
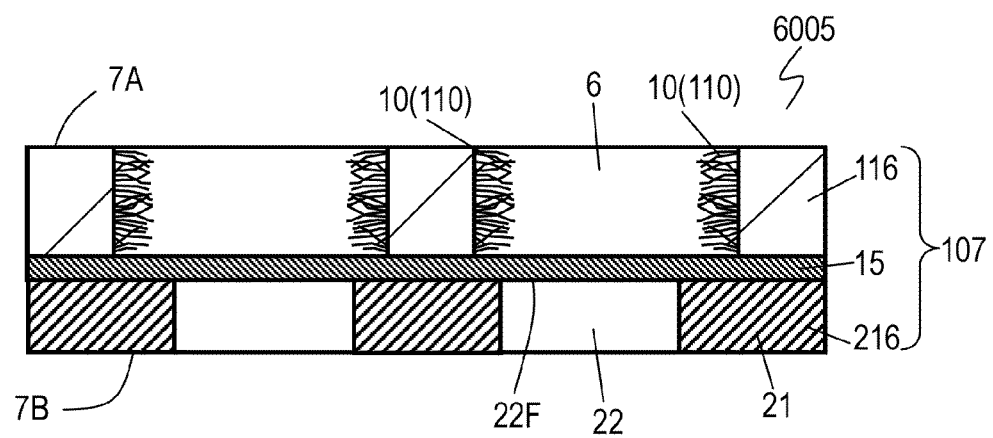
FIG. 16A is a sectional view of another flow channel structure according to Embodiment 3.

FIG. 16A is a sectional view of another flow channel structure 6005 according to Embodiment 3. In FIG. 16A, components identical to those of flow channel structure 5005 shown in FIG. 15 are denoted by the same reference numerals. Flow channel structure 6005 includes substrate 107, and the SOI substrate of Embodiment 2 shown in FIG. 11, instead of substrate 7 shown in FIG. 15. Substrate 107 has cavity 22 formed in surface 7B to expose a surface of silicon dioxide layer 15 through cavity 22. Silicon layer 216 constitutes base portion 21. Flow channel 6 and cavity 22 are formed by etching surface 7A of silicon layer 116 and surface 7B of silicon layer 216, respectively. Silicon dioxide layer 15 stops the etching, and makes the depths of flow channel 6 and cavity 22 constant.

The SOI substrate used for substrate 107 can be obtained readily since it is used to produce semiconductor devices. The thicknesses of silicon layers 116 and 216 and silicon dioxide layer 15 can be controlled.

Silicon dioxide layer 15 preferably essentially contains silicon dioxide, but may be made of any other material, such as glass, quartz, sapphires, or light-transmittable resin, having a light-transmittable property.

Figure 16B:
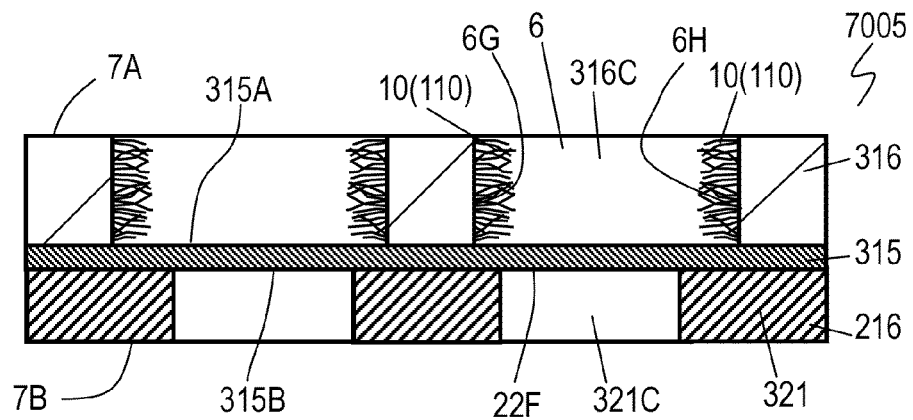
FIG. 16B is a sectional view of still another flow channel structure according to Embodiment 3.

FIG. 16B is a sectional view of still another flow channel structure 7005 according to Embodiment 3. In FIG. 16B, components identical to those of flow channel structures 5005 and 6005 shown in FIGS. 15 and 16 are denoted by the same reference numerals. As described above, flow channel structure 5005 shown in FIG. 15 can be formed by bonding together base portion 21, a substrate having a through-hole formed in an area of flow channel 6, and another substrate having a light-transmittable property and constituting a bottom plate portion to close the through-hole. Flow channel structure 7005 shown in FIG. 16B includes bottom plate portion 315 having surfaces 315A and 315B opposite to each other, sidewall substrate 316 disposed on surface 315A of bottom plate portion 315, and base portion 321 disposed on surface 315B of bottom plate portion 315. Sidewall substrate 316 is made of silicon having through-hole 316C that becomes flow channel 6 and constitutes sidewalls 6G and 6H surrounding flow channel 6. Flow channel 6 includes plural fibrous bristles 10 formed on sidewalls 6G and 6H. Base portion 321 has through-hole 321C therein that forms cavity 22. Bottom plate portion 315 preferably essentially contains silicon dioxide, but may be made of any other material, such as glass, quartz, sapphires, or light-transmittable resin, having a light-transmittable property. Bottom plate portion 315 made of one of these materials, sapphire for instance, allows flow channel structure 7005 to be formed by directly bonding together bottom plate portion 315, sidewall substrate 316, and base portion 321. Alternatively, sidewall substrate 316 and base portion 321 may be formed by depositing a predetermined thickness of polycrystalline silicon or amorphous silicon on surfaces 315A and 315B of bottom plate portion 315 by a vapor growth method, such as low-pressure chemical vapor deposition (LPCVD) method or a normal-pressure chemical vapor deposition (CVD) method.

Furthermore, the material of bottom plate portion 315 may be selected according to a wavelength of the light used for measurement of the substance that flows in flow channel 6. If visible light is used for the measurement, for instance, bottom plate portion 315 is made of glass. If the ultraviolet light is used, bottom plate portion 315 may be made of quartz or sapphire. As described, there are a variety of options in selecting the material of bottom plate portion 315 and the manufacturing method, and they are to be considered as not restricting the scope of the present invention.

A flow channel structure according to the present invention can homogenize a solution in the flow channel, and is therefore useful for a small and accurate chemical assay chip.

The invention claimed is:

1. A flow channel structure comprising:
   a substrate having a first surface having a flow channel formed therein, the flow channel having an inner wall made of silicon; and
   a plurality of fibrous bristles, consisting of amorphous silicon dioxide, extending from the inner wall of the flow channel,
   wherein the flow channel is configured to allow a solution to flow through the flow channel.

2. The flow channel structure according to claim 1, wherein the plurality of fibrous bristles have curled shapes tangle with one another.

3. The flow channel structure according to claim 1, wherein the plurality of fibrous bristles extend in a same direction.

4. The flow channel structure according to claim 1, wherein each of the plurality of fibrous bristles has branched twigs.

5. The flow channel structure according to claim 1,
   wherein the inner wall of the flow channel has a bottom and a sidewall extending from the bottom to the first surface of the substrate, and
   wherein the plurality of fibrous bristles extend from the bottom and the sidewall of the inner wall of the flow channel.

6. The flow channel structure according to claim 1, wherein each of the plurality of fibrous bristles includes:
   a plurality of cores made of metal; and
   molecules of silicon dioxide strung to respective ones of the plurality of cores.

7. The flow channel structure according to claim 6, wherein the plurality of cores are attached to the inner wall of the channel.

8. The flow channel structure according to claim 6, wherein the molecules made of silicon dioxide strung to respective ones of the plurality of cores are made of oxygen and the silicon of the inner wall of the flow channel.

9. The flow channel structure according to claim 6, wherein the metal is one of Pt, Fe, Co, Ni, and Au.

10. The flow channel structure according to claim 1, wherein the plurality of fibrous bristles extend in a direction parallel to a direction in which the solution flows through the flow channel.

11. The flow channel structure according to claim 1,
    wherein the flow channel includes:
    a plurality of inlet channels merging at a connecting portion; and
    a confluent flow channel extending from the connecting portion, and
    wherein the plurality of fibrous bristles are formed in the confluent flow channel.

12. The flow channel structure according to claim 1,
    wherein the inner wall of the flow channel has a bottom and a sidewall extending from the bottom to the first surface of the substrate, and
    wherein the substrate includes a bottom plate portion constituting the bottom of the flow channel, the bottom plate portion having a light-transmittable property.

13. The flow channel structure according to claim 12, wherein the bottom plate portion essentially contains silicon dioxide.

14. The flow channel structure according to claim 12,
wherein the substrate further has a second surface opposite to the first surface, and
wherein the substrate has a cavity formed in the second surface and opposite to the flow channel.

15. The flow channel structure according to claim 1,
wherein the inner wall of the flow channel includes a bottom, and
wherein the substrate includes:
    a sidewall substrate having a through-hole therein, the through-hole constituting the flow channel; and
    a bottom plate portion having a first surface bonded to the sidewall substrate to cover the through-hole, the bottom plate constituting the bottom of the flow channel, the bottom plate portion having a light-transmittable property.

16. The flow channel structure according to claim 15,
wherein the bottom plate portion further has a second surface opposite to the first surface,
wherein the substrate has a cavity formed in the second surface of the substrate opposite to the flow channel, and
wherein the substrate further includes a base portion bonded to the second surface at a position around the cavity.

17. The flow channel structure according to claim 1, wherein said flow channel structure consists essentially of said substrate and said plurality of fibrous bristles.

18. A flow channel structure comprising:
    a substrate having a first surface having a flow channel formed therein, the flow channel having an inner wall; and
    a plurality of fibrous bristles extending from the inner wall of the flow channel,
    wherein the plurality of fibrous bristles and the inner wall of the flow channel of the substrate are made of silicon compounds made of same elements, and wherein said fibrous bristles consist of amorphous silicon dioxide.

19. The flow channel structure according to claim 18, wherein said flow channel structure consists essentially of said substrate and said plurality of fibrous bristles.

20. A flow channel structure comprising:
    a substrate having a first surface having a flow channel formed therein, the flow channel having an inner wall; and
    a plurality of fibrous bristles extending from the inner wall of the flow channel,
    wherein the plurality of fibrous bristles and the inner wall of the flow channel of the substrate are made of silicon compounds made of same elements,
    wherein the flow channel is configured to allow a solution to flow through the flow channel, and wherein said fibrous bristles consist of amorphous silicon dioxide.

21. The flow channel structure according to claim 20, wherein said flow channel structure consists essentially of said substrate and said plurality of fibrous bristles.

* * * * *